United States Patent [19]

Klug et al.

[11] Patent Number: 5,068,434
[45] Date of Patent: Nov. 26, 1991

[54] PROCESS FOR THE PREPARATION OF N-ALKYLATED ANILINES

[75] Inventors: Günter Klug, Monheim; Hans-Josef Buysch, Krefeld; Lothar Puppe, Burscheid, all of Fed. Rep. of Germany

[73] Assignee: Bayer Aktiengesellschaft, Leverkusen, Fed. Rep. of Germany

[21] Appl. No.: 301,929

[22] Filed: Jan. 25, 1989

[30] Foreign Application Priority Data

Feb. 6, 1988 [DE] Fed. Rep. of Germany ....... 3803661

[51] Int. Cl.$^5$ ........................................... C07C 209/18
[52] U.S. Cl. .................................... 564/399; 564/401
[58] Field of Search ................. 564/399, 401; 502/64, 502/66, 71

[56] References Cited

U.S. PATENT DOCUMENTS

| | | | |
|---|---|---|---|
| 2,012,801 | 8/1935 | Andrussow et al. | 260/128 |
| 3,728,408 | 4/1973 | Tobias | 260/668 C |
| 3,957,874 | 5/1976 | Dockner et al. | 260/577 |
| 4,613,705 | 9/1988 | Hargis | 564/409 |
| 4,801,752 | 1/1984 | Chen et al. | 564/401 |
| 4,806,689 | 2/1989 | Gier et al. | 564/479 |

FOREIGN PATENT DOCUMENTS

2195350 8/1987 Japan .

OTHER PUBLICATIONS

Chen et al. II, Chem. Abst., "The Selective Alkylation of Aniline with Methanol over ZSM-5 Zeolite", vol. 107 (1987), 107:6705h.
Wu et al., Chem. Abst., "Alkylation of Aniline with Methanol over ZSM-5 and ADHM Zeolites", vol. 109 (1988), 109:75635p.
Patent Abstract of Japan Band 12, Nr. 47(C-475)(2894), 12.02.1988 & JP-A-62195350 (Idemitsu Kosan) 28.08.1987.
Chemical Abstracts Band 108, Nr. 3, 18.01.1988, Seite 558, Spalte 2, Zusammenfassung Nr. 21483y, Columbus, Ohio, US; & JP-A-62195350 (Idenitsu Kosan) 28.08.1987.
Chemical Abstracts Band 84, Nr. 17, 26. Apr. 1976, Seite 500, Spalte 1, Zusammenfassung Nr. 121339k, Columbus, US: Takamiya Nobuo et al.: "N-Methylation of Aniline with Methanol Over Transition Metal Zeolite"; & Waseda Daigaku Rikogaku Kenkyusho Hokoku 1975, Band 69, Seiten 21–25.
Chemical Abstracts Band 103, Nr. 17, 28. Oktober 1985, Seite 684, Spalte 1, Zusammenfassung Nr. 141538p, Columbus, Ohio, US; Onaka Makoto et al.: "Selective N-Monoalkylation of Aniline Derivatives by use of Alkali Cation Exchanges X-and Y-Type Zeolites."; & J. Inclusion Pehnom. 1984, 2(1-2) Seiten 359–366.
Chemical Abstracts Band 103, Nr. 2, 15, Juli 1985, Seite 75, Spaltel 1, Zusammenfassung Nr. 7725u, Columbus, Ohio, US; G.O. Chivadze et al.: "Alkylation of Aniline by Methanol on Modified Synthetic Zeolites."; & Izv. Akad. Nauk Gruz. SSR, Ser. Khim. 1984, 10(3) Seiten 232–234.
Chemical Abstracts Band 107, Nr. 1,6. Juli 1987, Seite 616, Spalte 1, Zusammenfassung Nr. 6705h, Columbus, Ohio, US; P.Y. Chen et al.: "The Selective Alkylation of Aniline with Methanol Over ZSM-5 Zeolite."; & Stud. Surf. Sci. Catal. 1986, 28(New Dev. Zeolite Sci. Technol.) Seiten 739–746(Kat. D).
Chemical Abstracts Band 109, Nr. 10,5 Sep. 1988, Seite 127, Spalte 1, Zusammenfassung Nr. 75635p, Columbus, Ohio, US; Kerui Wu et al.: "Alkylation of Aniline with Methanol Over ZSM-5 and ADHM Zeolites."; & Shiyou Huagong 1988(3) Seiten 135–138.

*Primary Examiner*—Richard L. Raymond
*Assistant Examiner*—Peter G. O'3 Sullivan
*Attorney, Agent, or Firm*—Sprung Horn Kramer & Woods

[57] ABSTRACT

N-alkylated anilines can be prepared by reaction of anilines with lower alcohols or dialkyl ethers at elevated temperature and in the presence of zeolite catalysts of the pentasil type containing protons and having an $SiO_2/Al_2O_3$ ratio of at least 60.

12 Claims, No Drawings

PROCESS FOR THE PREPARATION OF N-ALKYLATED ANILINES

BACKGROUND OF THE INVENTION

The present invention relates to a process for the preparation of N-alkylated anilines by reaction of anilines with lower alcohols or dialkyl ethers at elevated temperature and in the presence of proton-containing zeolites of the pentasil type having an $SiO_2/Al_2O_3$ ratio of at least 60.

N-alkylated anilines are important industrial intermediates for the preparation of dyestuffs, stabilizers, urethanes, ureas, pharmaceuticals and plant-protection agents. They are usually prepared by alkylation of anilines with alcohols in the presence of acidic catalysts, for example phosphorus oxychloride, under pressure or by passing aniline and alcohol vapors together through hot phosphoric acid at atmospheric pressure.

These processes are unsatisfactory in some respects. The reaction in an autoclave under pressure is industrially expensive, and the homogeneously dissolved acidic catalysts cause extensive corrosion. The phosphoric acid process at atmospheric pressure has this disadvantage to a lesser extent, the relatively large amount of phosphoric acid becomes unusable as a catalyst over time and has to be disposed of and replaced by fresh phosphoric acid.

It is true of both processes that they have only relatively little flexibility with respect to the alternating preparation of N-monoalkylanilines and N,N-dialkylanilines.

Zeolites have already been proposed as catalysts for these reactions, and it has been shown that both N-monoalkyl- and also N,N-dialkylanilines can be obtained. However, other disadvantages arise.

According to Waseda Daigaku Rikogaku Konkyusho Hokoku 69 (1975), 21-25 (cited in C.A. 84 (1976), 121 339 k), Y-zeolites and also H-Y as well as those exchanged with Cu, Ni, Co, Mn, Zn, Ca and Ce ions are suitable as catalysts for the reaction of methanol with aniline to give N-methylated anilines. However, from Table 1 on page 23 of this reference, it can be seen that all reactions are accompanied by the formation of toluidine, that is, by ring-alkylation. The highest activity (100 % of conversion) and one of the highest rates (86%) of N-methylation is shown by H-Y, however only at an uneconomical molar ratio of methanol: aniline=3:1. The highest N-methylation rate (92 %) is shown by Cu-Y, in which case, however, the conversion is significantly less (44.9%) and the formation of toluidine is still 3.4%.

In addition, the reaction on Cu-Y and H-Y has a very unfavorable temperature dependence, since a useful conversion is achieved only in a very narrow temperature range around 250° C. (cf. FIGS. 1 and 2 on page 22), whereas at other only slightly changed temperatures not only conversion but also yield in N-alkylated anilines decrease.

P. Y. Chen, M. C. Chen, H. Y. Chu, N. S. Chang and T. K. Chuang, Proc. 7th Intern. Zeolite Conf. Y. Murakami, A. Iijima and J. W Ward (Eds.), p. 739-744, Kodansha, Tokyo and Elsevier, Amsterdam, Oxford, New York, Tokyo 1986 show in their investigation of N-methylation of aniline with methanol on ZSM-5 zeolites that ring-alkylation is always observed and they are convinced that it is caused by active centers on the surface of the zeolites. Furthermore, not only the basic but also the acidic properties of the zeolites are said to have been responsible for catalytic activity in such a manner that upon impregnation of the zeolites with metal oxides ring-alkylation decreases. Yet, even under the most favorable conditions (table on p. 744) using MgO/H-ZSM 5, noticeable ring-alkylation is still found. In addition, a temperature of 350° C. and a large excess of methanol must be used. This indicates a very low activity of these zeolites. Furthermore, an increase in $SiO_2/Al_2O_3$ ratio results in decreasing conversion of aniline (FIG. 1 on p. 741). Admittedly, the selectivity increases but even in the most favorable case ring-alkylation still amounts to several % (FIG. 2 on p. 742). Consequently, the acidic H-ZSM 5 appears to be the least suitable zeolite. It almost produces the lowest aniline conversion and is rapidly deactivated (FIG. 3 on p. 743) and furthermore causes one of the highest ring-alkylation rates (Table 2 on p. 743).

SUMMARY OF THE INVENTION

Surprisingly it has now been found that protoncontaining zeolites of the pentasil type having an $SiO_2/Al_2O_3$ ratio of at least 60 represent significantly better catalysts for the N-alkylation of anilines with alcohols, cause only minor or practically no ring-alkylation, have improved service lives and accomplish good conversions even at a low alcohol/aniline ratio.

Accordingly, the invention relates to a process for the preparation of N-alkylated anilines of the formula

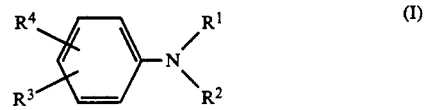

by reaction of anilines of the formula

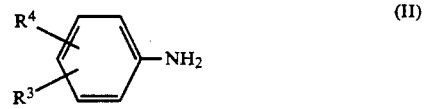

in which formulae $R^1$ denotes $C_1-C_4$-alkyl and $R^2$ denotes hydrogen or $C_1-C_4$-alkyl and $R^3$ and $R^4$ independently of one another stand for hydrogen, $C_1-C_4$-alkyl, $C_1-C_4$-alkoxy, fluorine, chlorine or bromine with $C_1-C_4$-alcohols or the corresponding dialkyl ethers in the presence of zeolites at elevated temperature, which is characterized in that the zeolites used are those of the pentasil type containing protons and having an $SiO_2/Al_2O_3$ ratio of at least 60.

DETAILED DESCRIPTION OF THE INVENTION

Suitable anilines for the process according to the invention are those of the formula (II), for example aniline or the isomeric toluidines, fluoroanilines, chloroanilines, bromoanilines, xylidenes, ethylanilines, isopropylanilines and others which result from (II). Preference is given to those anilines in which $R^{11}=C_1-C_2$-alkyl alkyl and $R^{12}$=hydrogen or $C_1-C_2$-alkyl take the place of $R^1$ and $R^2$. Further preferred anilines are those in which $R^{13}$ and $R^{14}$ independently of one another denoting hydrogen, $C_1-C_2$-alkyl, $C_1-C_2$-alkoxy, fluorine or chlorine, preferably $R^{23}$ and $R^{24}$ denoting independently of one another hydrogen, $C_1$-$C_2$-alkyl or chlorine, take the place of $R^3$ and $R^4$.

Examples of alkylating agents suitable for the process according to the invention are dimethyl ether, diethyl ether, methanol, ethanol, propanol, isopropanol, butanol or isobutanol, preferably methanol and ethanol.

The reactants can be diluted by inert gases such as nitrogen or water vapor or by inert solvents such as hydrocarbons, for example pentane, cyclohexane, methylcyclohexane, isooctane, benzene, toluene, xylene, cumene or ethylbenzene.

Suitable zeolites for the process according to the invention are pentasils containing protons and belonging to the formula

$$H(M_{m/z})[mAlO_2 \cdot nSiO_2] \cdot qH_2O \qquad (III)$$

in which n/m, calculated as the $SiO_2/Al_2O_3$ ratio, is at least 60, $(M_{m/z})$ represents the metal cations present in the pentasil as replacement for some of the hydrogen ions, z indicates the valence of these cations and q indicates the amount of water phase adsorbed.

The $SiO_2/Al_2O_3$ ratio is, for example, 60 to 2,000, preferably 70 to 1,500, particularly preferably 80 to 1,000.

Examples of preferred pentasils are ZSM 5, ZSM 11, ZSM 8, ZSM 5/ZSM 11-intermediates, zeta 1, zeta 3, ZBM 10, ultrasil, ultrazet, TZ-01, NU-4, NU-5 and AZ-1. Pentasils of the type ZSM 5, ZSM 8, ZSM 11 and ZSM 5/ZSM 11-intermediates are particularly preferred. Pentasils of the ZSM 5 type are very particularly preferred. The preparation of these pentasil types is known. Reference can be made to D. W. Breck: Zeolite Molecular Sieves, John Wiley and Sons Inc., New York 1974, Russ. J. Phys. Chem. 55 (1981), 1175 and European Patents 18,090, 34,727, 54,386, 57,016, 65,401, 113,116, DE-OS (German Published Specification) 2,548,697, DE-OS (German Published Specification) 2,643,929, U.S. Pat. No. 3,702,886, U.S. Pat. No. 3,709,979 and GB Patent 1,334,243.

The pentasil zeolites suitable for the process according to the invention can contain exclusively protons as the cations. However, up to 80 equivalent % of the protons can also be substituted by other ions. The ions suitable for this purpose are, for example, those of sodium, potassium, magnesium, zinc, cobalt, copper, calcium, iron, the rare earths (for example cerium, lanthanum), tin, manganese, chromium, titanium, zirconium, tantalum and others. Preferably, a maximum of 50 equivalent %, particularly preferably a maximum of 25 equivalent %, very particularly preferably a maximum of 10 equivalent % and most preferably a maximum of 5 equivalent %, of the protons are substituted in the pentasils by others of the metal cations mentioned.

The reaction of the process according to the invention can be carried out batchwise with stirring in liquid phase and under the resulting pressure, it being possible for the pentasil zeolites to be used in compact or in powdered form. The amount of pentasil is 2 to 50% by weight, preferably 5 to 40% by weight, particularly preferably 7 to 30% by weight, relative to the total weight of the batch.

Furthermore, the reaction can be carried out continuously in the gas phase. In this type of operation, the reaction can be in particular carried out at atmospheric pressure. Such a continuous operation is preferred for industrial application. For this purpose, an aniline/alcohol vapor mixture which is undiluted or diluted with inert gas or inert vapor is passed over a catalyst bed of penlasil zeolite present in grain form. The space velocity can in this case be varied within wide limits. Good conversions are obtained by adjusting the space velocity in the range from 0.01 to 8.0, preferably 0.05 to 5.0, particularly preferably 0.1 to 4.0 liters, of mixture to be reacted liter of catalyst/hour.

To convert the pentasil zeolites into a compact form, which is favorable for the operation of a gas phase reactor, they are compacted with binders and granulated. Suitable binders are various clays, aluminosilicates and aluminum oxides, in particular $\gamma$-$Al_2O_3$ and $SiO_2$. These binders are used in amounts of 15 to 50% by weight, relative to the ready-to-use zeolite catalysts.

The reaction temperature is 220° to 370° C., preferably 240° to 350° C., particularly preferably 260° to 330° C.

The ratio of aniline to alcohol is largely variable. However, it also determines which ratio of N-monoalkylated to N,N-dialkylated anilines are obtained in the reaction product. Thus, an amount of 0.5 to 3 roles of alcohol/mole of aniline can in general be used, preferably 0.7 to 2 moles. If a high percentage of N-monoalkylated aniline is desired, the reaction should be carried out at a molar ratio alcohol: aniline of 0.5:1.2, preferably 0.7:1.0.

EXAMPLE 1

10 moles each of aniline and methanol were dissolved in 1.5 ml of benzene and, after the addition of 0.25 g of one of the zeolites mentioned, the mixture was heated at 300° C. for 3 hours. Table I below contains more detailed data of the individual experiments and the results obtained.

Examples 1.1 to 1.5 are according to the invention and show high selectivities of N-methylation at a high aniline conversion. Depending on the molar ratios of aniline/methanol, high selectivities of N-monomethylation (1.1, 1.2, 1.4) or N,N-dimethylation (1.3) could be obtained. Comparative Examples 1.6 and 1.7 have high ringalkylation rates under the same conditions.

EXAMPLE 2

A reaction tube, about 20 mm in diameter, was charged with 20 g of zeolite granules having an average particle size of 1 to 2 mm. A mixture of aniline and methanol vapor was passed over these zeolite granules at different space velocities and different temperatures for several hours. Exact conditions and results of these experiments are listed in Table II. According to Examples 2.1 and 2.2, selective N-methylation could also be obtained in the gas phase reaction at atmospheric pressure. Even after 35 hours of operation, no change in the activity of the H-ZSM 5 zeolite took place in Example 2.3. Even at an extremely high $SiO_2/Al_2O_3$ ratio, a high selectivity with respect to N-alkylation (Example 2.4) was still obtained. A higher supply of aniline significantly improved the selectivity with respect to N-monoalkylation (Example 2.5), which gave evidence of the flexibility of the process according to the invention. It is true that Comparative Example 2.6 under comparable conditions using a non-acidic Na-ZSM 5 gave a good selectivity of N-methylation, but it gave only a completely inadequate conversion. It is true that at higher temperatures it was possible to increase the conversion according to the abovementioned prior art, but at the same time the percentage of ring-alkylation was also increased.

tion conditions too little conversion, ring-alkylation and rapid deactivation (Comparative Example 3.3).

TABLE I

| No. | Catalyst | SiO$_2$/Al$_2$O$_3$ | Molar ratio Aniline/MeOH | Product Distribution in % by weight | | | |
|---|---|---|---|---|---|---|---|
| | | | | A | NMA | NNDMA | ring-alk A |
| 1.1 | H-ZSM 5 | 100 | 1:1 | 15 | 62 | 23 | <0.3 |
| 1.2 | Sn-ZSM 5 | 100 | 1:1 | 26 | 55 | 19 | <0.3 |
| 1.3 | H-ZSM 5 | 100 | 1:7 | 0.5 | 5 | 93 | 1.8 |
| 1.4 | H-ZSM 5 | 100 | 0.5:1 | 54 | 40 | 6 | <0.1 |
| 1.5 | H-ZSM 11 | 110 | 1:1 | 33 | 49 | 17 | <1 |
| 1.6 | H-Y | 4.9 | 1:7 | 2.8 | 1 | 65 | 30 |
| 1.7 | Ca-Y | 4.8 | 1:1 | 28 | 42 | 18 | 12 |

A = Aniline
NAM = Monomethylaniline
NNDMA = N,N-dimethylaniline
MeOH = Methanol

TABLE II

| No. | Catalyst | SiO$_2$/Al$_2$O$_3$ | Molar ratio A/MeOH | Temp. °C. | Space velocity ml/ml/h | Time on stream h | Product distribution in % by weight | | | |
|---|---|---|---|---|---|---|---|---|---|---|
| | | | | | | | A | NMA | NNDMA | ring-alk A |
| 2.1 | H-ZSM 5 + 30% γ-Al$_2$O$_3$ | 107 | 1:1 | 300 | 0.5 | 5 | 30 | 40 | 29 | <0.4 |
| 2.2 | H-ZSM 5 + 30% γ-Al$_2$O$_3$ | 107 | 1:1 | 280 | 0.5 | 5 | 40 | 36 | 24 | <0.1 |
| 2.3 | H-ZSM 5 + 15% SiO$_2$ | 107 | 1:1 | 290 | 0.6 | 35 | 46 | 34 | 10 | 0 |
| 2.4 | H-ZSM 5 + 30% γ-Al$_2$O$_3$ | 800 | 1:1 | 300 | 1.0 | 4 | 48 | 32 | 19 | <1 |
| 2.5 | H-ZSM 5 + 30% γ-Al$_3$O$_3$ | 107 | 2:1 | 300 | 1.0 | 7 | 60 | 31 | 9 | 0 |
| 2.6 | Na-ZSM 5 + 30% γ-Al$_2$O$_3$ | 107 | 1:1 | 300 | 1.0 | 3 | 85 | 10 | 5 | <0.3 |

EXAMPLE 3

The procedure as described in Example 2 was repeated. However, the alkylating agent used was ethanol and it was used in a molar ratio of aniline:ethanol=1:1. All reactions were carried out at 300° C. and at a space velocity of the catalyst of 1.0 ml/ml/h (see Table III).

Using ethanol also gave a high selectivity in N-alkylation (3.1 and 3.2). N-monoalkylation under the same conditions turned out to be higher in this case than in the N-methylation. The Y-aluminum oxide by itself, which was used as binder material, has under the reac-

EXAMPLE 4

Under the conditions of Example 3, m-toluidine was reacted with ethanol.

Using H-ZSM 5, the expected virtually 100% N-alkylation and no reduction in catalyst activity after 100 hours were found (4.1).

In Comparative Example 4.2 using H-Y, a considerable percentage of m-toluidine was, as already shown in Example 1.5, alkylated on the ring.

TABLE III

| No. | Catalyst | SiO$_2$/Al$_2$O$_3$ | Time on stream | Product distribution in % by weight | | | |
|---|---|---|---|---|---|---|---|
| | | | | A | NEA | NNDEA | ring-alkyl.A |
| 3.1 | H-ZSM 5 + 15% of SiO$_2$ | 107 | 4 | 48 | 48 | 4 | 0.1 |
| 3.2 | H-ZSM 5 + 30% of γ-Al$_2$O$_3$ | 107 | 4 | 41 | 52 | 6 | <1.5 |
| 3.3 | γ-Al$_2$O$_3$ | — | 4 | 77 | 20 | — | 3 (rapid deactivation) |

NEA = N-ethylaniline
NNDEA = N,N-diethylaniline

TABLE IV

| No. | Catalyst | SiO$_2$/Al$_2$O$_3$ | Time on stream h | Space velocity ml/ml/h | Product distribution in % by weight | | | |
|---|---|---|---|---|---|---|---|---|
| | | | | | mT | NET | NNDET | ring-alkyl.T |
| 4.1 | H-ZSM 5 + 30% of γ-Al$_2$O$_3$ | 107 | 100 | 1.3 | 43 | 52 | 5 | <0.1 |
| 4.2 | H-Y + 30% of γ-Al$_2$O$_3$ | 4.6 | 4 | 1.0 | 34 | 50 | 6 | 10 | mT = m-toluidine
NET = N-ethyl-m-toluidine
NNDET = N,N-diethyl-m-toluidine

What is claimed is:

1. A process for the preparation of an N-alkylated aniline of the formula

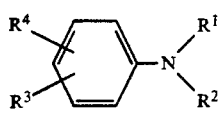

comprising reacting an aniline of the formula

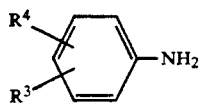

in which formulae
- $R^1$ denotes $C_1$-$C_4$-alkyl
- $R^2$ denotes hydrogen or $C_1$-$C_4$-alkyl, and
- $R^3$ and $R^4$ independently of one another stand for hydrogen $C_1$-$C_4$-alkyl,
- $C_4$-alkyl $C_1$-$C_4$-alkoxy, fluorine, chlorine or bromine, with a $C_1$-$C_4$-alcohol or the corresponding dialkyl ethers in the presence of a zeolite at elevated temperature, the improvement wherein the zeolite is of the pentasil type and is selected from the group consisting of ZSM 5, ZSM 8, ZSM 11, or ZSM 5/ZSM 11-intermediates containing protons, having 0 to 25 equivalent % of the protons exchanged for sodium, potassium, magnesium, zinc, cobalt, copper, calcium, iron, rare earths, tin, manganese, chromium, titanium, zirconium and/or tantalum, and having an $SiO_2/Al_2O_3$ of 80 to 1000 and wherein the pentasil zeolite is compacted with a binder and granulated and wherein the reaction is carried out at a temperature from 220° to 370° C.

2. The process of claim 1, wherein the pentasil is a ZSM 5 type.

3. The process of claim 1, wherein 0 to 10 equivalent % of the protons are exchanged.

4. The process of claim 3, wherein 0 to 5 equivalent % of the protons are exchanged.

5. The process of claim 1, wherein, if the reaction is carried out batchwise in the liquid phase, 2 to 50% by weight of pentasil zeolite, relative to the total weight of the batch, are used.

6. The process of claim 5, wherein 5 to 40% by weight of pentasil zeolite are used.

7. The process of claim 6, wherein 7 to 30% by weight of pentasil zeolite are used.

8. The process of claim 1, wherein, if the reaction is carried out continuously in the gas phase, the space velocity is adjusted in the range from 0.01 to 8.0 liters of mixture to be reacted/liter of catalyst/hour.

9. The process of claim 8, wherein space velocity is adjusted in the range from 0.05 to 5.0 liters of mixture to be reacted liter of catalyst/hour.

10. The process of claim 9, wherein the space velocity is adjusted in the range from 0.1 to 4.0 liters of mixture to be reacted/liter of catalyst/hour.

11. The process of claim 1 wherein the reaction is carried out at a temperature from 240 to 350° C.

12. The process of claim 1, wherein the binder is clay, aluminosilicate or aluminum oxide.

UNITED STATES PATENT AND TRADEMARK OFFICE
CERTIFICATE OF CORRECTION

PATENT NO. : 5,068,434

DATED : November 26, 1991

INVENTOR(S) : Klug et al.

It is certified that error appears in the above-identified patent and that said Letters Patent is hereby corrected as shown below:

| | |
|---|---|
| Title Page | U.S.PATENT DOCUMENTS: After " 4,613,705, 9/ " delete " 1988 " and substitute -- 1986 --, after " 4,801,752, 1/ " delete " 1984 " and substitute -- 1989 --. |
| Col. 7, line 22 | Delete " $C_4$-alkyl " |
| Col. 7, last line | After " $SiO_2/Al_2O_3$ " insert -- ratio -- |

Signed and Sealed this

First Day of June, 1993

Attest:

MICHAEL K. KIRK

Attesting Officer

Acting Commissioner of Patents and Trademarks